United States Patent
Hong et al.

(10) Patent No.: US 11,893,662 B2
(45) Date of Patent: Feb. 6, 2024

(54) DENSITY COMPENSATION FUNCTION IN FILTERED BACKPROJECTION

(71) Applicant: Northwestern University, Evanston, IL (US)

(72) Inventors: Kyungpyo Hong, Rego Park, NY (US); Daniel Kim, Naperville, IL (US)

(73) Assignee: Northwestern University, Evanston, IL (US)

( * ) Notice: Subject to any disclaimer, the term of this patent is extended or adjusted under 35 U.S.C. 154(b) by 380 days.

(21) Appl. No.: 17/393,061

(22) Filed: Aug. 3, 2021

(65) Prior Publication Data

US 2022/0044453 A1  Feb. 10, 2022

Related U.S. Application Data (60) Provisional application No. 63/060,832, filed on Aug. 4, 2020.

(51) Int. Cl.
*G06T 11/00* (2006.01)
*G01R 33/48* (2006.01)
*G01R 33/56* (2006.01)

(52) U.S. Cl.
CPC ........ *G06T 11/006* (2013.01); *G01R 33/4824* (2013.01); *G01R 33/5608* (2013.01);
(Continued)

(58) Field of Classification Search
CPC . G06T 11/006; G06T 11/008; G06T 2210/41; G06T 2211/421; G01R 33/4824;
(Continued)

(56) References Cited

U.S. PATENT DOCUMENTS

| | | | |
|---|---|---|---|
| 6,748,098 B1* | 6/2004 | Rosenfeld | G06T 3/4007 600/410 |
| 7,187,794 B2* | 3/2007 | Liang | G06T 5/002 378/4 |

(Continued)

FOREIGN PATENT DOCUMENTS

| | | | | |
|---|---|---|---|---|
| CN | 108693491 A | * | 10/2018 | ........... A61B 5/0042 |
| CN | 109581253 B | * | 5/2021 | ............ G01R 33/48 |

(Continued)

OTHER PUBLICATIONS

Zeng, GL., "Revisit of Ramp Filter," *IEEE Trans Nucl Sci.* (Feb. 2015), vol. 62, No. 1; pp. 131-136. DOI:10.1109/TNS.2014.2363776.

(Continued)

*Primary Examiner* — Mahendra R Patel
(74) *Attorney, Agent, or Firm* — Bell & Manning, LLC (57) ABSTRACT

An imaging system includes a sensor configured to receive imaging data, where the imaging data comprises k-space data from a magnetic resonance imaging (MRI) scan of a patient. The imaging system also includes a processor operatively coupled to the sensor and configured to identify a degree of interaction between measured points of the k-space data located at a radius from a center of k-space. The processor is also configured to determine, based at least in part on the degree of interaction between the measured points, density weights for a density compensation filter. The processor is also configured to apply the density compensation filter to the k-space data to generate filtered k-space data. The processor is further configured to generate an MRI image of the patient based at least in part on the filtered k-space data.

15 Claims, 9 Drawing Sheets

(52) U.S. Cl.
CPC ........ *G06T 11/008* (2013.01); *G06T 2210/41* (2013.01); *G06T 2211/421* (2013.01)

(58) Field of Classification Search
CPC .... G01R 33/5608; G01R 33/56; A61B 6/5258
USPC ........................................................ 382/131
See application file for complete search history.

(56) References Cited

U.S. PATENT DOCUMENTS

| | | | | |
|---|---|---|---|---|
| 7,345,283 | B2* | 3/2008 | Gunter | G06T 11/006 250/369 |
| 7,653,229 | B2* | 1/2010 | Kaufhold | G06T 11/006 382/154 |
| 7,737,406 | B2* | 6/2010 | Vija | G01T 1/1611 250/363.04 |
| 8,908,942 | B2* | 12/2014 | Zeng | G06F 18/00 382/128 |
| 10,890,641 | B2* | 1/2021 | Wang | A61B 5/0042 |
| 2001/0027262 | A1* | 10/2001 | Mistretta | G01R 33/563 600/9 |
| 2007/0096732 | A1* | 5/2007 | Samsonov | G01R 33/5611 324/309 |
| 2008/0012562 | A1* | 1/2008 | Beatty | G01R 33/5611 324/307 |
| 2010/0039110 | A1* | 2/2010 | Takahashi | G01R 33/5611 382/280 |
| 2011/0142316 | A1* | 6/2011 | Wang | G06T 11/006 382/131 |
| 2015/0192653 | A1* | 7/2015 | Sharif | A61B 5/0044 600/420 |
| 2018/0360384 | A1* | 12/2018 | Lai | A61B 5/7214 |
| 2020/0333416 | A1* | 10/2020 | Moeller | G01R 33/5608 |

FOREIGN PATENT DOCUMENTS

| | | | | |
|---|---|---|---|---|
| JP | 2008295925 | A | * 12/2008 | |
| WO | WO-2007085342 | A1 | * 8/2007 | ........... G01R 33/482 |
| WO | WO-2007124151 | A2 | * 11/2007 | ............. A61B 5/055 |

OTHER PUBLICATIONS

Jackson JI, et al., "Selection of a Convolution Function for Fourier Inversion Using Gridding," *IEEE Transactions on Medical Imaging*, vol. 10, No. 3, Sep. 1991; pp. 473-478.

Pipe JG, et al., "Sampling Density Compensation in MRI: Rationale and an Iterative Numerical Solution," *Magnetic Resonance in Medicine* (1999), vol. 41; pp. 179-186.

Johnson KO, et al., "Convolution Kernel Design and Efficient Algorithm for Sampling Density Correction," *Magnetic Resonance in Medicine* (2009), vol. 61; pp. 439-447.

* cited by examiner

Fig. 1

| Parameter | Phantom | Real-time Cine | Cardiac perfusion |
|---|---|---|---|
| Field of view (FOV) | 288 x 288 mm² | 300 x 300 mm² | 300 x 300 mm² |
| Slice thickness | 8 mm | 6 mm | 8 mm |
| Image matrix | 192 x 192 | 160 x 160 | 192 x 192 |
| Spatial resolution | 1.5 x 1.5 mm² | 1.88 x 1.88 mm² | 1.56 x 1.56 mm² |
| Magnetization preparation | - | - | Saturation recovery [26] |
| TE/TR | 1.84/4.08 msec | 1.5-1.57/2.8-3.2 msec | 1.5/2.6 msec |
| Receiver bandwidth | 744 Hz/pixel | 780 Hz/pixel | 700 Hz/pixel |
| Readout | GRE | b-SSFP | GRE |
| Flip angle | 15° | 70° | 12° |
| Temporal resolution | - | 30.2-35.2 msec | - |
| # of projections | 600 | 1650 (11 per frame) | 1740 (30 per frame) |
| Projection angle | 111.246° | 32.040° | 23.628° |
| Angle range | 0 to 360° | 0 to 180° | 0 to 180° |

| Parameter | Standard DCF | Modified SL filter | Optimal DCF |
|---|---|---|---|
| SSIM (0=no match; 1=perfect match) | 0.94 | 0.94 | 0.94 |
| Blur Metric (0=sharp; 1=blur) | 0.30 | 0.33 | 0.31 |
| NRMSE (%) | 2.06 | 2.56 | 2.16 |

| Image | Parameter | No DCF | Standard DCF | Modified SL filter | Optimal DCF |
|---|---|---|---|---|---|
| Real-time Cine (11 projections per frame with 150 frames) | Process Time (sec) | 767.2 ± 140.9 | 1080.6* ± 115.5 | 924.8 ± 183.4 | 685.8†‡ ± 84.2 |
| | Data Fidelity | 0.0052 ± 0.0024 | 0.0061 ± 0.0028 | 0.0057 ± 0.0028 | 0.0055 ± 0.0026 |
| | SSIM | - | 0.97 ± 0.011 | 0.96 ± 0.012 | 0.99†‡ ± 0.005 |
| | NRMSE (%) | - | 0.43 ± 0.13 | 0.45 ± 0.14 | 0.27†‡ ± 0.06 |
| Cardiac perfusion (30 projections per frame with 58 frames) | Process Time (sec) | 584.6 ± 95.1 | 473.6* ± 69.5 | 434.1* ± 79.7 | 382.3* ± 126.9 |
| | Data Fidelity | 0.0095 ± 0.0057 | 0.0099 ± 0.0060 | 0.0098 ± 0.0059 | 0.0097 ± 0.0059 |
| | SSIM | - | 0.93 ± 0.013 | 0.94 ± 0.016 | 0.96†‡ ± 0.012 |
| | NRMSE (%) | - | 0.53 ± 0.11 | 0.49 ± 0.11 | 0.40†‡ ± 0.11 |

DENSITY COMPENSATION FUNCTION IN FILTERED BACKPROJECTION

CROSS-REFERENCE TO RELATED APPLICATION

The present application claims the priority benefit of U.S. Provisional Patent App. No. 63/060,832 filed on Aug. 4, 2020, the entire disclosure of which is incorporated by reference herein.

REFERENCE TO GOVERNMENT RIGHTS

This invention was made with government support under R01HL116895, R01HL138578, R21EB024315, R21AG055954, R01HL151079, R01HL117888, and R21EB030806 awarded by the National Institutes of Health (NIH). The government has certain rights in the invention.

BACKGROUND

Filtered backprojection (FBP) is a widely used analytic image reconstruction method for medical imaging modalities such as computed tomography (CT), single-photon emission computed tomography (SPECT), positron emission tomography (PET), magnetic resonance imaging (MRI) with radial k-space sampling, and the like. A ramp filter, or density compensation function (DCF), is a key component in FBP to remove blurring artifacts, but at the expense of noise amplification and streak artifacts. These two noted limitations (i.e., noise amplification and streaking artifacts) result in suboptimal implementation of DCF in FBP.

SUMMARY

An illustrative imaging system includes a sensor configured to receive imaging data, where the imaging data comprises k-space data from a magnetic resonance imaging (MRI) scan of a patient. The imaging system also includes a processor operatively coupled to the sensor and configured to identify a degree of interaction between measured points of the k-space data located at a radius from a center of k-space. The processor is also configured to determine, based at least in part on the degree of interaction between the measured points, density weights for a density compensation filter. The processor is also configured to apply the density compensation filter to the k-space data to generate filtered k-space data. The processor is further configured to generate an MRI image of the patient based at least in part on the filtered k-space data.

In some embodiments, the processor is further configured to convert the filtered k-space data from a polar coordinate system to a Cartesian coordinate system using gridding such that the conversion results in gridded k-space data with uniform density weights across k-space. In an illustrative embodiment, the density weights are uniform or substantially uniform. As used herein in this context, substantially refers to density weights that are within 1% variance of one another, within 2% variance of one another, within 4% variance of one another, etc. In such an embodiment, the processor can generate the MRI image of the patient based at least in part on the filtered and gridded k-space data by performing Fourier transform. Also, the processor is further configured to perform an inverse non-uniform Fourier transform based at least in part on the filtered k-space data. In an illustrative embodiment, the degree of interaction is based at least in part on an arc distance between the measured points at the radius. The degree of interaction can also be based at least in part on a distance criterion, where the distance criterion is Nyquist distance or 1. In one embodiment, the k-space data is received in the form of a 2-dimensional or 3-dimensional Fourier transform.

Another illustrative imaging system includes a sensor configured to receive imaging data, where the imaging data includes projection data for a computed tomography (CT) scan, a single-photon emission computerized tomography (SPECT) scan, or a positron emission tomography (PET) scan of a patient. The imaging system also includes a processor operatively coupled to the sensor and configured to identify a degree of interaction between measured points of the projection data located at a radius from a center of a projection space. The processor is also configured to determine, based at least in part on the degree of interaction between the measured points, density weights for a density compensation filter. The processor is also configured to apply the density compensation filter to the projection data to generate filtered projection data.

In an illustrative embodiment, the processor is further configured to back-project the filtered projection data from a polar coordinate system to a Cartesian coordinate system such that the back-projection results in a CT image, a SPECT image, or a PET image of the patient. The processor can also be further configured to generate a CT image, a SPECT image, or a PET image of the patient based at least in part on the filtered projection data. In some embodiments, the CT image, the SPECT image, or the PET image of the patient is generated based at least in part on an inverse Radon transform. The degree of interaction can be based at least in part on an arc distance between the measured points at the radius. The degree of interaction can also be based at least in part on a distance criterion, where the distance criterion is a sensor-to-sensor distance or 1. The sensor-to-sensor distance can be the distance between two consecutive sensors in a 1-dimensional sensor array to receive a single projection data. In other embodiments, the projection data is received in the form of a 2-dimensional or 3-dimensional Radon transform.

An illustrative method for reconstructing an image includes receiving, by a transceiver of a computing system, imaging data, wherein the imaging data comprises k-space data or projection data resulting from a scan of a patient. The method also includes identifying, by a processor of the computing system, a degree of interaction between measured points of the k-space data or measured points of the projection data. The method also includes determining, by the processor and based at least in part on the degree of interaction between the measured points, density weights for a density compensation filter. The method also includes applying, by the processor, the density compensation filter to the projection data to generate filtered projection data or to the k-space data to generate filtered k-space data. The method further includes generating, by the processor, an image of the patient based at least in part on the filtered projection data or the filtered k-space data.

In some embodiments, generating the image of the patient includes performing an inverse non-uniform Fourier transform on the k-space data or an inverse Radon transform on the projection data. In other embodiments, determining the degree of interaction includes determining an arc distance between the measured points at the radius. Determining the degree of interaction can also include determining a distance criterion, where the distance criterion is 1 in a discrete environment.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Tomographic imaging modalities such as computed tomography (CT), single-photon emission computed tomography (SPECT), positron emission tomography (PET), and magnetic resonance imaging (MRI) are considered among the most important medical inventions in the last 50 years, with each modality having strengths and weaknesses. While the physics of these various imaging techniques are vastly different, what they share in common is a digitalized image reconstruction pipeline including analytical and/or iterative algorithms.

The MRI procedure was first introduced in 1973, and was described in terms of radial k-space sampling and projection reconstruction. Shortly after this introduction of MRI, techniques such as slice-selection and echo-planar imaging on a Cartesian grid were discovered. Since these discoveries, the field has since moved towards Cartesian k-space sampling as the default sampling scheme for the vast majority of MRI protocols in radiology practice. Cartesian k-space sampling is favored over radial k-space sampling due to several advantages: (a) lower sensitivity to magnetic gradient field imperfections and static magnetic field variations, (b) higher sampling efficiency, and (c) simpler image reconstruction using discrete Fourier transform (DFT). However, despite its weaknesses, radial k-space sampling provides several advantages over Cartesian k-space sampling, including: (a) better motion properties, (b) more benign aliasing artifacts with undersampling, (c) capability to perform self-gating of physiologic signals such as electrocardiogram or respiratory motion, and (d) capability to reconstruct multi-contrast MRI by applying a band-pass filter to the oversampled center of k-space.

Backprojection is a canonical projection reconstruction method for CT, SPECT, PET, and polar MRI. Conventional backprojection, however, produces blurry images due to oversampling at the center of the projection space. This can be compensated by performing filtered backprojection (FBP) incorporating a density compensation filter. A standard density compensation filter (DCF) in FBP (e.g. ramp filter) is analytically determined by a linear transformation from polar to Cartesian coordinates. Because the standard DCF, which is a v-shaped high-pass filter, assigns a zero at the center, it results in reduced signal-to-noise ratio (SNR) and increased streaking artifacts. Both consequences may be partially addressed by assigning a non-zero value at the center of DCF or iteratively solving for a DCF tailored to a specific polar k-space sampling scheme in MR.

As noted above, in some implementations, a ramp filter can be used in filtered backprojection reconstruction. The ramp filter is a v-shaped high-pass filter that was developed to handle analog signals, but is being used in today's digital environment with little to no modification, even in highly undersampled acquisitions. A major limitation of a standard ramp filter is that it excludes the center of measured data (i.e., DC gain), which is the most important k-space content in MRI. Described herein is a novel ramp filter that accounts for all sampling schemes, including highly-undersampled acquisitions, and achieves a uniform density throughout the gridded Cartesian space. This technology is broadly applicable for all medical imaging modalities (CT, MRI, SPECT, PET) using filtered backprojection.

Iterative reconstruction or compressed sensing (CS) methods are widely used in CT, SPECT, PET, and MRI to produce high image quality from subsampled data. In cardiovascular MRI, radial k-space sampling offers several advantages over Cartesian k-space sampling, including: (a) better motion properties, (b) more benign aliasing artifacts with undersampling, (c) capability to perform self-gating of physiological signals such as electrocardiogram or respiratory motion. Because of said advantages, radial k-space sampling with an emphasis on acceleration has been making a comeback over the last two decades. An advantage in CS reconstruction of radial k-space data is that a DCF is not needed. A major disadvantage of CS is its lengthy processing time. One approach to accelerate CS reconstruction of radial k-space data is applying a DCF, but at the expense of reconstruction error. Thus, there is a need to develop an optimal DCF that accelerates CS reconstruction of subsampled radial k-space data without significant loss in image quality.

Described herein are methods and systems to analytically calculate an optimal DCF based on the Nyquist distance and geometrical properties of a polar coordinate system in a discrete space, regardless of sampling conditions (e.g., sampling rate and projection view angles). Several analyses were performed to compare the performance between standard and optimal DCFs in FBP of a phantom data obtained at the Nyquist sampling rate, where Cartesian k-space sampling is used as the reference. The performance between standard and optimal DCFs in CS reconstruction of subsampled real-time cine and first-pass cardiac perfusion MRI datasets obtained with irregular radial projection angles was also compared, where CS reconstruction without DCF is used as the reference. The proposed techniques are designed to accelerate CS reconstruction of subsampled radial k-space MRI data using an optimal DCF without significant loss in image quality compared with the reference reconstruction.

The new DCF described herein is broadly applicable for all radial sampling schemes, including highly-accelerated scans. The proposed DCF achieves a uniform density across the gridded radial data in the discrete environment. The theoretical basis of the proposed DCF is described below, along with experiments that compare the performance between the proposed DCF and a standard DCF on a T1 Mapping and Extracellular volume Standardization (TIMES) phantom and real-time cine and first-pass cardiac perfusion MRI datasets obtained from patients with various heart diseases.

To provide a proof-of-concept, the inventors briefly revisited the theory of 2D inverse Fourier transform (FT) in filtered backprojection. In filtered backprojection, a standard DCF |r| is an invariant 'v-shaped' continuous high-pass filter that is analytically derived as a Jacobian determinant describing a linear transformation from polar to Cartesian coordinate systems. This transformation can be described by the Fourier slice theorem described below in Equation 1:

$$f(x,y) = \int_0^\pi [\int_{-\infty}^\infty F_\theta(r)|r|e^{i2\pi r(x\cos\theta + y\sin\theta)} dr] d\theta,\quad \text{Equation 1:}$$

where f (•) is a projection reconstruction, x and y describe the pixel position in the image domain, $F_\theta(\theta)$ is the Fourier transform of a radial projection at an azimuthal angle θ, and r is a distance from the center of a radial projection. The general form of its discretization including a standard DCF is described below in Equation 2:

$$\rightarrow f(x, y) = \sum_\theta \left[ \frac{1}{M} \sum_{r=-M/2}^{M/2-1} F_\theta(r) \frac{2}{M}|r|e^{i2\pi \frac{r}{M}(x\cos\theta + y\sin\theta)} \right], \quad \text{Equation 2}$$

where M is the number of discrete samples in a radial projection. This transformation, however, may be insufficient in many instances when using a standard DCF, because only the property in the radial direction is translated into the discrete environment without consideration of other properties. For example, $$\frac{2}{M}|r|$$

is invariant, regardless of the number of projections or the variations in azimuthal angles.

In an ideal imaging condition meeting the Nyquist sampling requirement $$\left( = \frac{\pi}{2} \times \text{samples in a projection} \right),$$

a standard invariant v-shaped In in the above equations produces aliasing artifact-free results. However, the signal-to-noise ratio (SNR) is lower for radial than a Cartesian equivalent because the center of k-space is set to zero in the radial scan by standard DCF, as described in more detail below. Noise amplification caused by high-pass filtering of the standard DCF will be even worse in accelerated radial MRI scans. It was hypothesized that the invariant ramp filter should be flexibly adapted for gridding radial data from polar onto Cartesian coordinate systems in the discrete sampling meeting Nyquist or below/above Nyquist condition.

To test the hypothesis, an optimal DCF formulation is proposed herein that geometrically solves the non-uniform density of gridded radial k-space data, where the goal is to make the density across gridded radial k-space data to be uniform as they are in Cartesian k-space sampling. Specifically, described herein is a novel formulation to calculate an optimal DCF by leveraging the Nyquist distance in the radial and circumferential directions of the polar coordinate system. This new formula, i.e., DCF (r, θ), directly correlates to radial distances from the origin in the projection space or k-space, as well as azimuthal angles of the scanned projections as described below (Equation 3):

$$f(x, y) = \sum_\theta \left[ \frac{1}{M} \sum_{r=-M/2}^{M/2-1} F_\theta(r) DCF(r, \theta) e^{i2\pi \frac{r}{M}(x\cos\theta + y\sin\theta)} \right]. \quad \text{Equation 3}$$

The discrete samples are uniformly spaced along its radial projection direction. In MRI, the sample spacing corresponds to the Nyquist distance δk=1/field of view (FOV). In CT, PET, and SPECT, the sample spacing corresponds to the sensor-to-sensor distance of an 1-D detector array. For convenience, this uniform spacing of 1-D projection along the radial direction is defined as discrete unit radial distance (Δr)=1. The spacing of discrete samples, when gridded onto a polar coordinate system along the circumferential direction, i.e., arc distance (L)=∫rdθ=rΔθ, varies with radius. A new framework is introduced herein to make the Nyquist arc distance along the circumferential direction at a given radius r to be equal to the Nyquist distance along the radial projection direction such that Δr=discrete unit arc distance (ΔL)=1. By definition, this spacing satisfies the Nyquist sampling condition for each of two directions.

Figure 1:
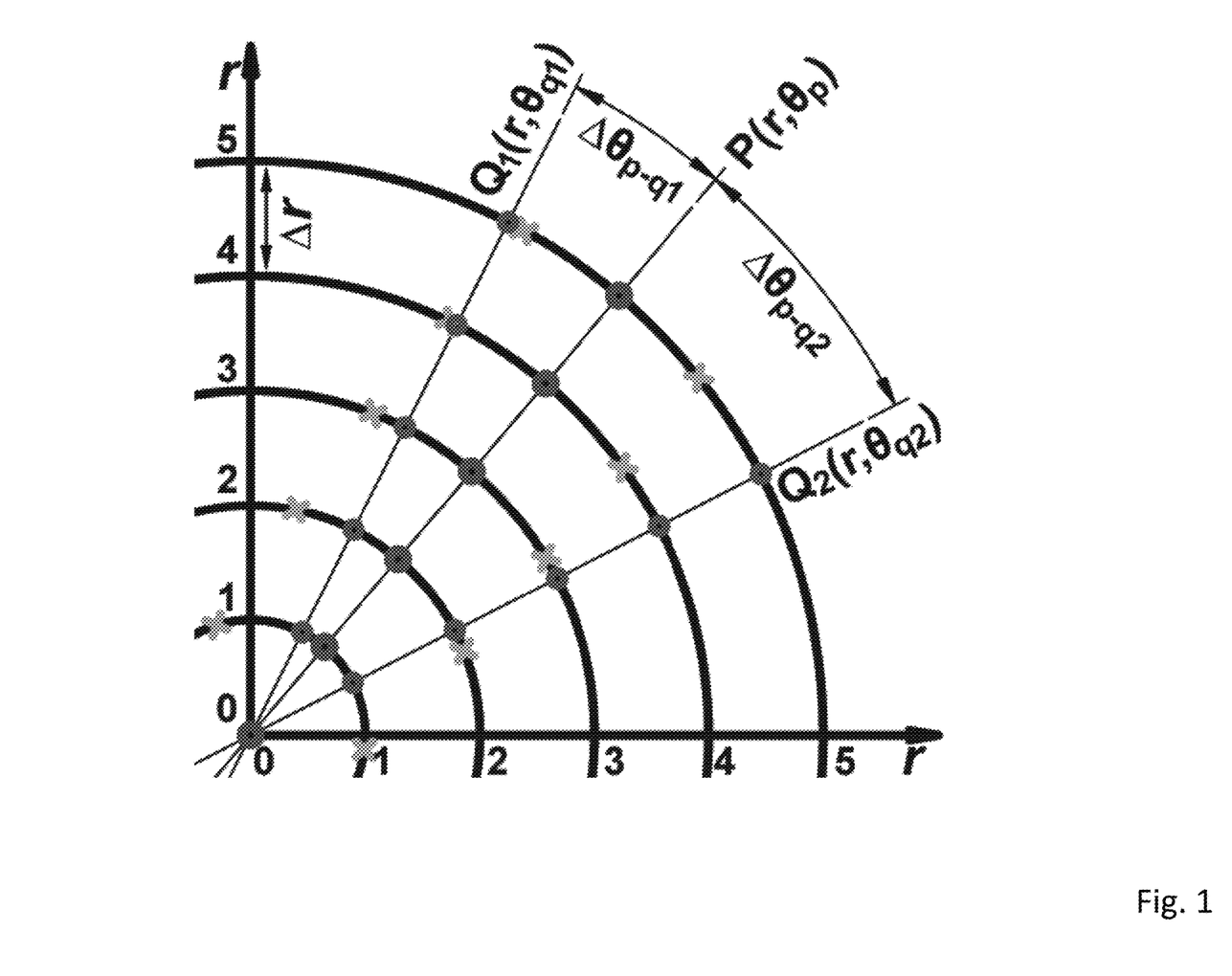
FIG. 1 depicts optimal DCF in a polar coordinate system in accordance with an illustrative embodiment.

FIG. 1 depicts optimal DCF in a polar coordinate system in accordance with an illustrative embodiment. In the figure, P(r, $\theta_p$) represents the projection of interest with dots (i.e., on P) to calculate DCFs. $Q_1$(r, $\theta_{q1}$) and $Q_2$ (r, $\theta_{q2}$) represent the P's neighboring projections with dots (i.e., on $Q_1$ and $Q_2$) to be considered for the P's DCF calculations. The crosses in FIG. 1 represent the pairs of Nyquist arc distances from P(r, $\theta_p$): i.e., P(r, $\theta_p$−ΔL) and P(r, $\theta_p$+ΔL) at each radius. For example, at r=2, $Q_1$ and $Q_2$ are located within the pair of crosses, whereas at r=3, only $Q_1$ exists within the pair. The corresponding DCFs can be calculated using the proposed formula, in equations 4 and 5 below. In addition, at r=5, P has no overlap with $Q_1$ and $Q_2$, except an overlap with itself resulting in overlap$_{pp}{}^5$=ΔL−L=1−5|$\theta_p$−$\theta_p$|=1 and DCF(5, $\theta_p$)=1. The values Δr=discrete unit radial distance=1; ΔL=discrete unit arc distance=1; L=measured arc distance; θ=azimuthal angle; Δ=difference.

The framework of FIG. 1 is used to calculate the degree of overlaps at a given point P(r, $\theta_p$) with all other points Q(r, $\theta_q$) along the circumferential direction. When a neighboring data point Q(r, $\theta_q$) is located within the range of P's arc spacing, P(r, $\theta_p$−ΔL)<Q(r, $\theta_q$)<P(r, $\theta_p$+ΔL), the degree of its overlap (Overlap$_{pq}{}^r$) is determined as the difference of the discrete unit arc distance, ΔL, and the measured arc distance, L, between P(r, $\theta_p$) and Q(r, $\theta_q$). The overlap equals 1 (i.e., 100%) if the two points are at the same location; otherwise, it is less than 1. This calculation is repeated for each point P(r, $\theta_p$) with all neighboring points along the circumferential direction (i.e. rung) including itself. Finally, DCF(r, $\theta_p$) is calculated as inversely proportional to the sum of all degrees of overlaps including itself as described in the equations below:

$$\begin{cases} Overlap_{pq}^r = \Delta L - L = 1 - r|\theta_p - \theta_q|, & \text{if } L < \Delta L \\ Overlap_{pq}^r = 0, & \text{otherwise} \end{cases}$$

Equation 4

$$\begin{cases} DCF(r, \theta_p) = 1 \Big/ \sum_{q=1}^{2N_{rp}} Overlap_{pq}^r, & \text{if } r = 1, 2, \ldots, M/2 - 1 \\ DCF(0, \theta_p) = 1 \big/ N'_{rp} & \text{if } r = 0 \end{cases}$$

Equation 5

In the equations above, $Overlap_{pq}^r$ is the degree of overlap between two neighboring data points at r of $p^{th}$ and $q^{th}$ radial projection, $\theta_p$ and $\theta_q$ are the azimuthal angles of $p^{th}$ and $q^{th}$ radial projection, respectively, $N_{rp}$ is the number of scanned radial projections, and M is the number of sampled data points in a radial projection. It is noted that the range of p and q is from 1 to $2N_{rp}$, because the sampled data points of a radial projection are symmetric at the origin of the projection space. It is also noted that the individual overlap is 1 at r=0, because all central data points of radial projections are located at the origin: i.e., L=0.

Three different DCFs were compared: a) standard DCF (e.g., ramp filter), b) modified Shepp-Logan (SL) filter, and c) optimal DCF. For the standard DCF, the value $$\frac{2}{M}|r|$$

was used, as described by equation 2. For the optimal DCF, equations 4-5 were used. For the modified SL filter, a standard DCF was multiplied by a sinc function (i.e., SL filter) and a non-zero value was assigned at the center of projections (for consistency, the same value as in the optimal DCF).

For visual comparison of DCFs, the inventors calculated DCFs for all projections, summed up the DCFs (i.e., sum-of-DCF), and plotted the sum as a function of the radius r, where Nyquist sampling per radius was added as a reference (sum of DCF(r, θ)≅2×πr). For convenience, the normalized sum-of-DCFs by Nyquist sampling was also plotted. This theoretical analysis was conducted to reflect the phantom and patient MRI experiments described below: (a) 600 golden angle (GA) projections representing the phantom experiment, (b) 11 tiny golden angle (TGA) projections representing the real-time cine MRI experiment, and (c) 30 TGA projections representing the cardiac perfusion MRI experiment.

MRI experiments were conducted on two 1.5 Tesla (T) whole-body MRI scanners (MAGNETOM Aera and Avanto, Siemens Healthcare, Erlangen Germany), equipped with a gradient system capable of creating a maximum gradient strength of 45 mT/m and a maximum slew rate of 200 mT/m/ms. A body coil was used for radio-frequency (RF) excitation, and standard body flex and spine coil arrays (18 or 30 elements) were used for signal reception. In alternative implementations, different hardware and/or values may be used.

Figure 2:
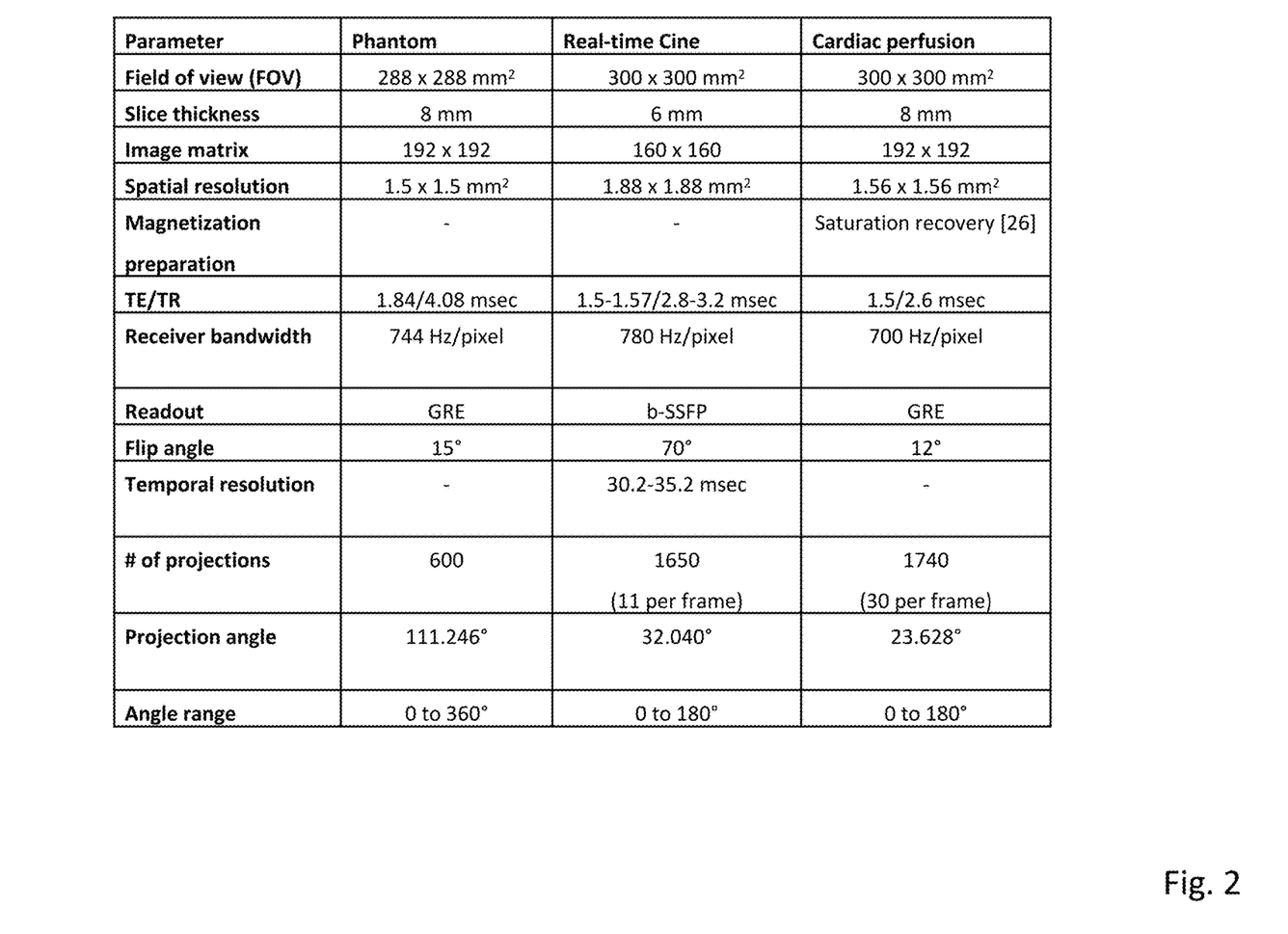
FIG. 2 is a table that summarizes the relevant MRI imaging parameters used in the phantom and in-vivo experiment in accordance with an illustrative embodiment.

To conduct a phantom experiment, the inventors scanned a medical device-grade T1 phantom (TIMES) using a gradient echo pulse sequence. A fully sampled radial k-space data (600 radial projections for 192×192 reconstruction matrix) was acquired using Golden angles (GA) (111.256°). As reference, the corresponding Cartesian k-space data was acquired with matching 600 k-space lines (average=3 plus 4% oversampling in the phase-encoding direction). FIG. 2 is a table that summarizes the relevant MRI imaging parameters used in the phantom experiment in accordance with an illustrative embodiment. In FIG. 2, GRE refers to gradient echo readout and b-SSFP refers to balanced steady state free precession readout.

In this study, 20 patients (17 males; 66.3±11.5 years) were scanned using a 14.5-fold accelerated, real-time cine MRI pulse sequence with $5^{th}$ Fibonacci sequence of tiny golden angles (TGA) (32.040°). Nineteen different patients (17 males; 51.4±16.0 years) were scanned using a 6.4-fold accelerated, cardiac perfusion MRI pulse sequence with $7^{th}$ Fibonacci sequence of TGA (23.628°). The perfusion scan was performed at rest with a bolus administration of 0.1 mmol/kg of gadobutrol (Gadavist, Bayer HealthCare Whippany, USA) at the rate of 3 mL/s, followed by a 20 mL saline flush. All scans were performed during free-breathing. As discussed above, the relevant imaging parameters are summarized in the table of FIG. 2.

Image reconstruction was performed using GPU-accelerated non-uniform fast Fourier transform (gpu-NUFFT) on a GPU workstation (V100 Tesla GPU with 16 GB memory, NVIDIA, Santa Clara, California, USA; Xeon ES-2620 2.10 GHz with 256 GB memory, Intel, Santa Clara, California, USA) equipped with MATLAB (R2020b, the MathWorks, Natick, Massachusetts, USA). In alternative embodiments, the image reconstruction may be performed using different hardware. During the pre-processing step, the inventors performed auto-calibrated gradient delay correction using a Radial Intersections (RING) method, and utilized its calculated coefficients for phase correction in each radial projection. For the fully-sampled TIMES phantom k-space data, FBP was performed using coil-by-coil, gpu-NUFFT, and the individual singe-coil NUFFT images were combined by the sum-of-square method.

For the subsampled k-space datasets of patients, a radial CS sensitivity encoding (SENSE) framework was employed using multi-coil, gpu-NUFFT. After removal of streaking coils based on visual inspection, coil compression was performed using principal component analysis (PCA) to produce 10 virtual coils. Coil sensitivities were self-calibrated by performing additional processing on the time-average image. For consistency, the same coil sensitivities derived from optimal DCF were applied for all iterative reconstructions. For iterative CS, a temporal total variation (TTV) was used as the sparsifying transform and nonlinear conjugate gradient with back-tracking line search was used as the optimization algorithm with a stop criterion set at 0.001% relative difference in image domain between pre- and post-iteration. The regularization weight was 0.05% of maximal signal for standard DCF and modified SL filter; 0.1% of maximal signal for optimal DCF and no DCF; the maximum signal was updated for each iteration. The regularization weight was empirically established by sweeping over a range from 0.005 to 0.5 (0.05 steps) and identifying the regularization weight that achieves a good balance between suppression of aliasing artifacts and temporal blurring of myocardial wall motion. This optimal regularization weight was determined based on visual inspection of six training datasets. For the conjugate gradient with DCFs, $\nabla f(x)$ was modified by inserting the DCF function: $\nabla f(x) = 2F_u^*(DCF(r, \theta)(F_u x - y))$. During CS reconstruction, the data fidelity and processing time for each iteration were recorded.

For the phantom images, the inventors calculated NRMSE, blur metric (1=blurriest; 0=sharpest), and structural similarity index (SSIM; 1=perfect match; 0=no match), where the Cartesian image was used as reference. Also, the background was masked using thresholding. For the patient images, SSIM and NRMSE were calculated, where CS images reconstructed without DCF were used as a reference, and images were cropped to exclude the background (i.e. heart region only).

Statistical analyses were conducted using MATLAB. The inventors tested for normality of variables using the Shapiro-Wilk test. Either one-way analysis of variance (ANOVA) (normal distribution) or Kruskal-Wallis test (non-parametric) was used to detect differences in mean measurements (i.e., process time, data fidelity, SSIM, NRMSE) among DCFs (no DCF, standard DCF, modified SL filter, optimal DCF), with Bonferroni correction for each pair analysis. A value of p<0.05 was considered statistically significant.

Figure 3:
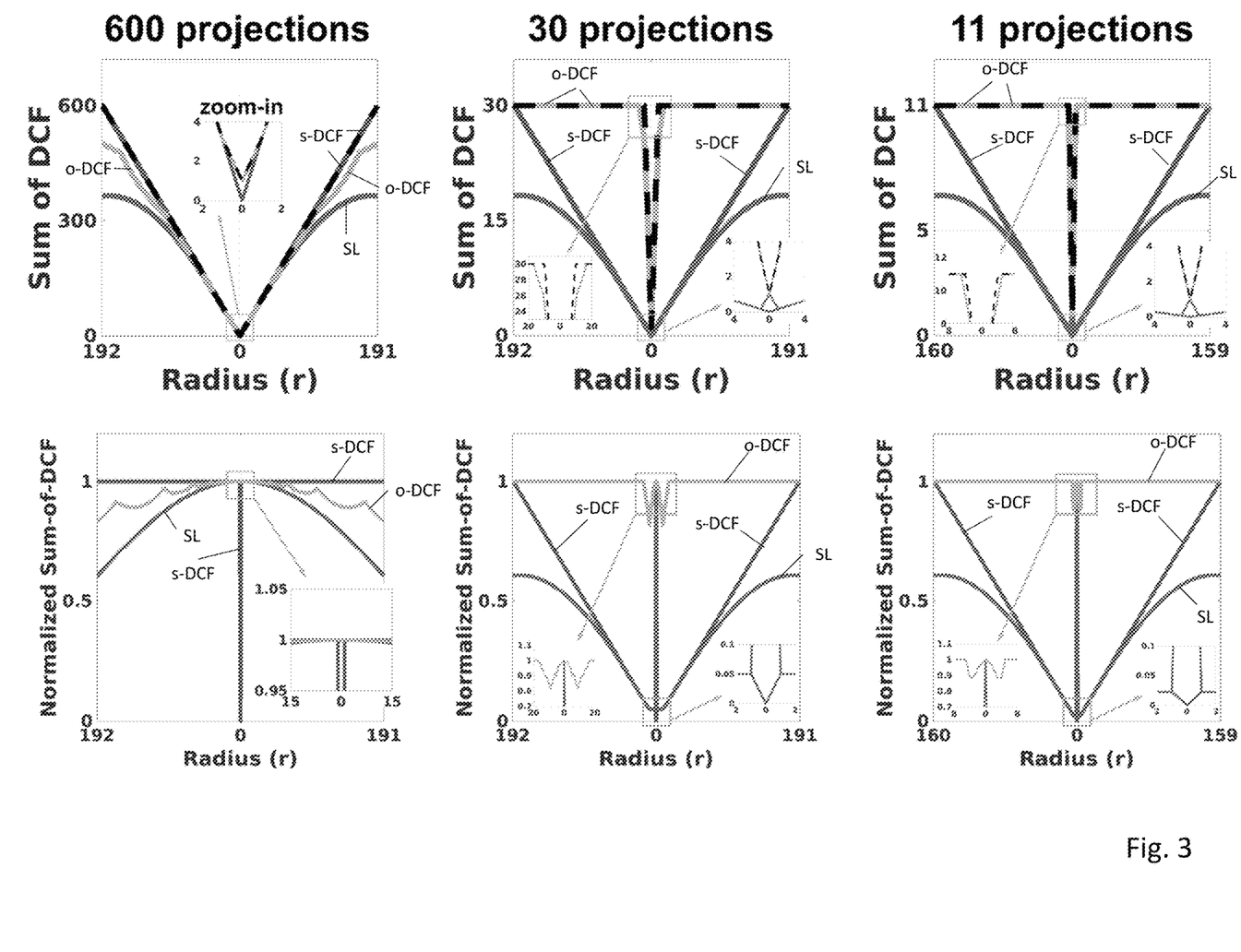
FIG. 3 depicts plots of sum-of-DCF and its normalized sum-of-DCF (by Nyquist sampling) for the analysis in accordance with an illustrative embodiment.

FIG. 3 depicts plots of sum-of-DCF and its normalized sum-of-DCF (by Nyquist sampling) for the analysis in accordance with an illustrative embodiment. Specifically, FIG. 3 depicts plots of the sum of DCFs and normalized sum-of-DCFs (divided by Nyquist sampling) for standard DCF, a modified SL filter, and optimal DCF. As shown, for 600 radial projections (phantom), compared with Nyquist sampling (black dashed line), standard DCF (s-DCF) is perfectly aligned everywhere except at the origin (which is the most important region in k-space). The modified SL filter (SL) is perfectly aligned near the origin but is considerably misaligned at the outer radius. The optimal DCF (o-DCF) is perfectly aligned near the origin and only slightly misaligned at the outer radius. For 30 radial projections (cardiac perfusion) and 11 radial projections (real-time cine), optimal DCF is nearly perfectly aligned with Nyquist sampling throughout, whereas both standard and modified SL filter were misaligned throughout. In FIG. 3, the radius r represents the distance from the center of the projections. According to the Shapiro-Wilk test, the process times of real-time cine and cardiac perfusion were not normally distributed (statistic: [0.81, 0.85]; p<0.01), whereas others were normally distributed (statistic: [0.93, 0.97]; p>0.05).

Figure 4:
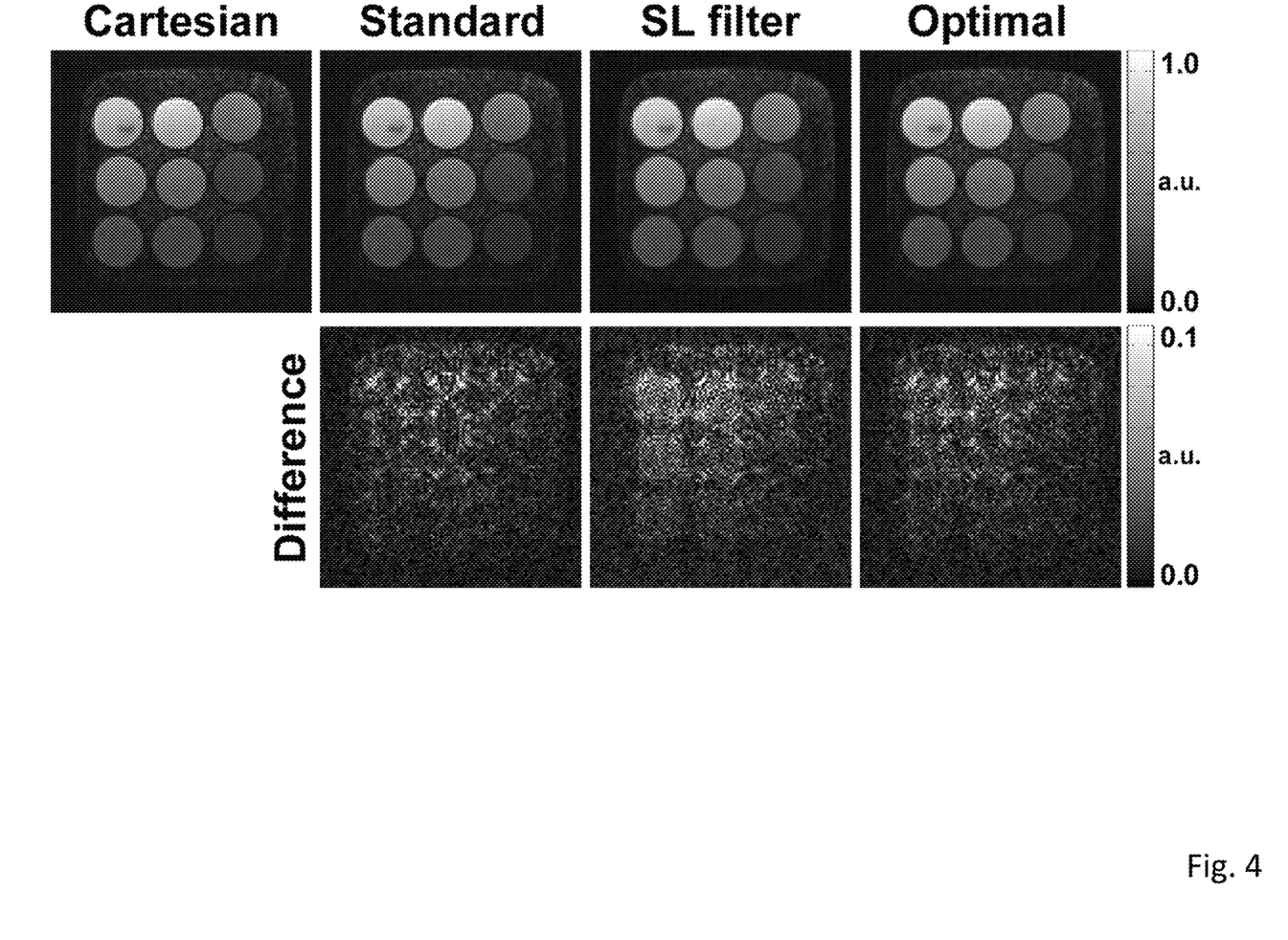
FIG. 4 depicts the TIMES phantom images reconstructed using FBP at the Nyquist sampling rate with standard DCF, modified SL filter, and optimal DCF in accordance with an illustrative embodiment.
Figure 5:
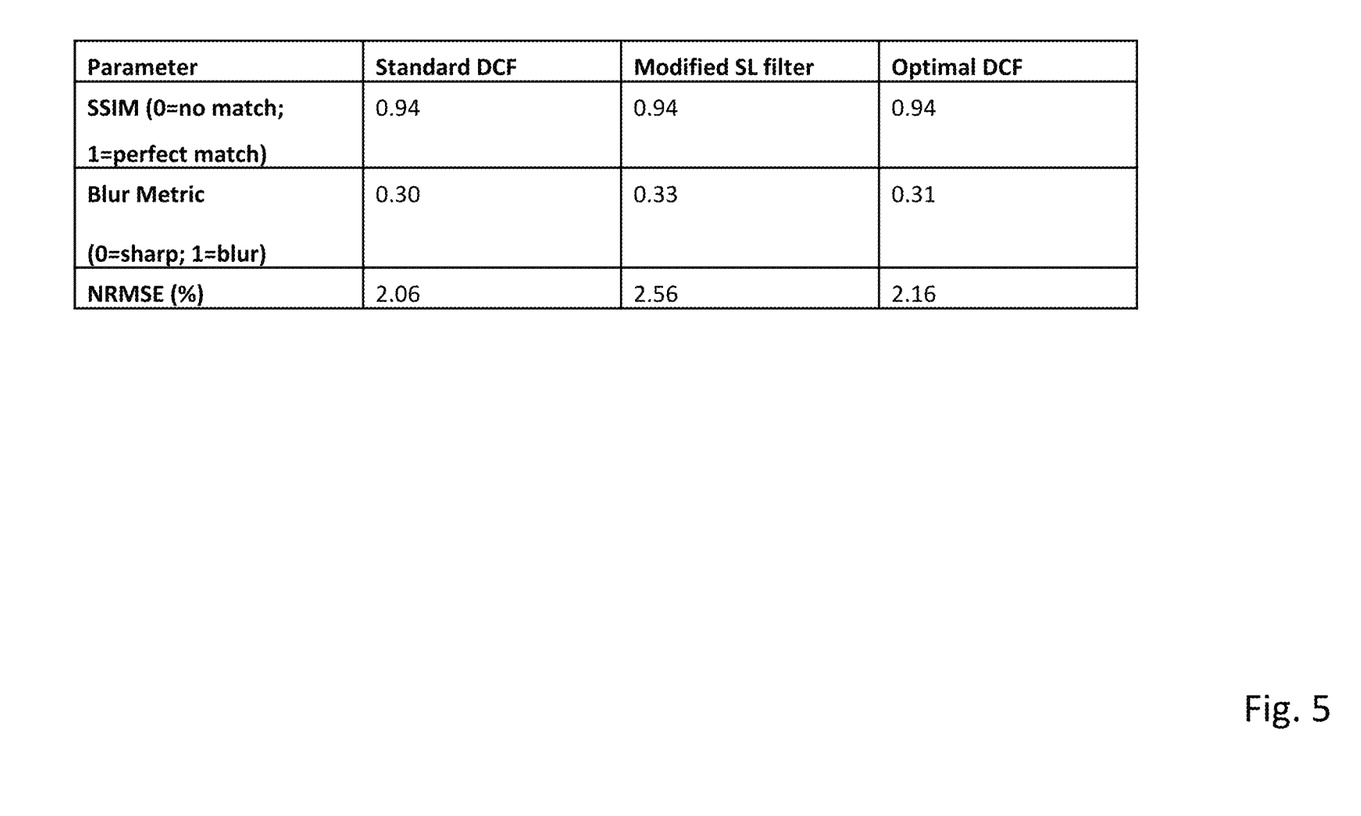
FIG. 5 is a table that summarizes a comparison of the NRMSE, SSIM, and blur metrics with the Cartesian reference in accordance with an illustrative embodiment.

FIG. 4 depicts the TIMES phantom images reconstructed using FBP at the Nyquist sampling rate with standard DCF, modified SL filter, and optimal DCF in accordance with an illustrative embodiment. The first column of FIG. 4 shows Cartesian k-space sampling, the second column shows standard DCF, the third column shows use of a modified SL filter, and the fourth column shows optimal DCF. FIG. 4 also shows the difference images compared with the Cartesian as the reference. The difference images were displayed 10 times narrower grayscale to bring out the differences. FIG. 5 is a table that summarizes a comparison of the NRMSE, SSIM, and blur metrics with the Cartesian reference in accordance with an illustrative embodiment. The data of FIG. 5 confirms that the proposed optimal DCF produces uniform densities in the gridded k-space at the Nyquist sampling rate. It is noted that the blur metric of the Cartesian reference was 0.27.

Figure 6:
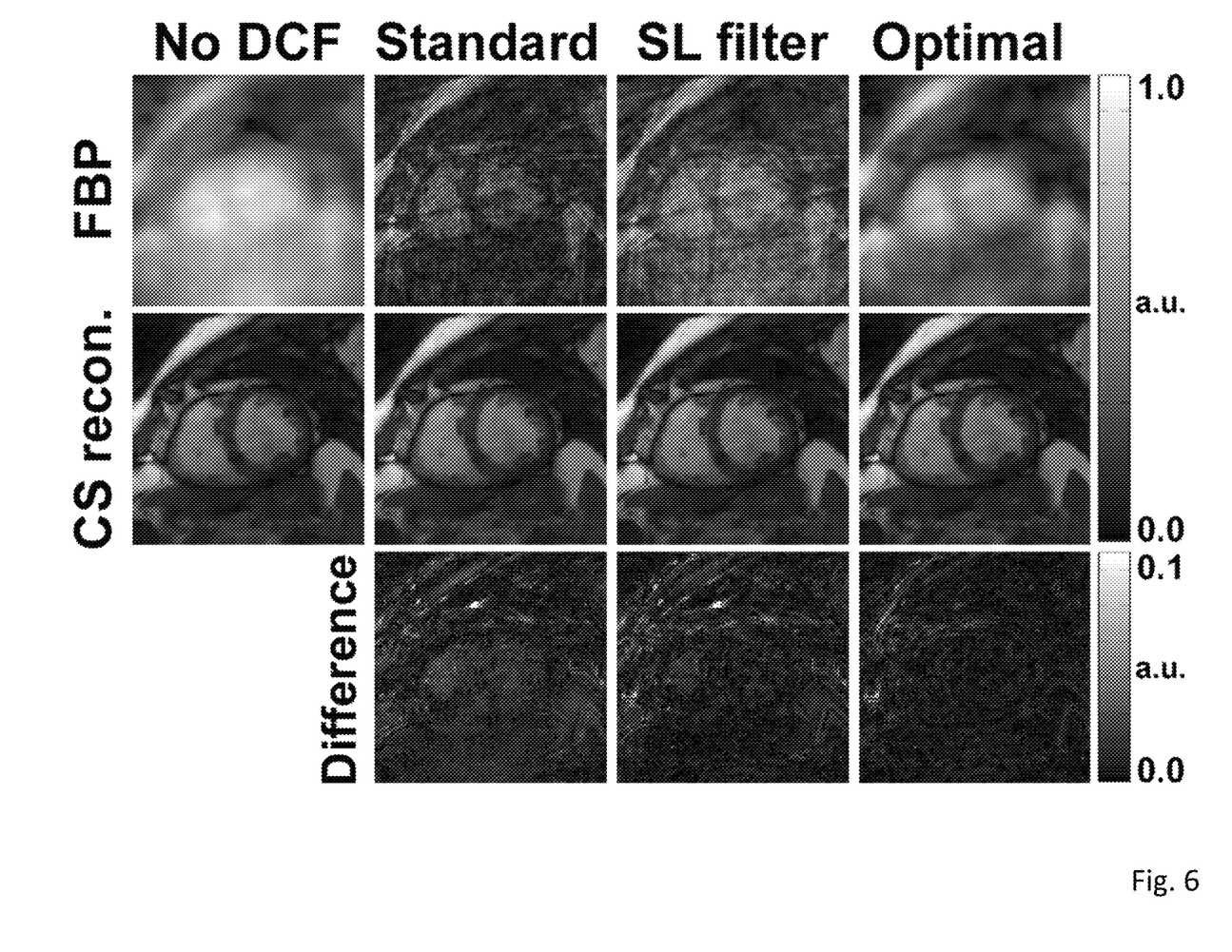
FIG. 6 shows real-time cine images of a patient reconstructed using FBP (i.e. zero-filled NUFFT) and CS by four different DCFs (none [reference], standard, modified SL filter, optimal) in accordance with an illustrative embodiment.

FIG. 6 shows real-time cine images of a patient reconstructed using FBP (i.e. zero-filled NUFFT) and CS by four different DCFs (none [reference], standard, modified SL filter, optimal) in accordance with an illustrative embodiment. FIG. 6 also shows the difference images compared with the reference. While all four reconstructions produced similar image quality, the difference images show that optimal DCF produced higher reconstruction accuracy than other DCFs. In FIG. 6, the corresponding SSIM was 0.97, 0.97, and 0.99 for standard DCF, modified SL filter, and optimal DCF, respectively. The corresponding NRMSE was 0.50%, 0.44%, and 0.28% for standard DCF, modified SL filter, and optimal DCF, respectively. Also, it is noted that the difference images are displayed 10-times narrower grayscale to bring out differences.

Figure 7:
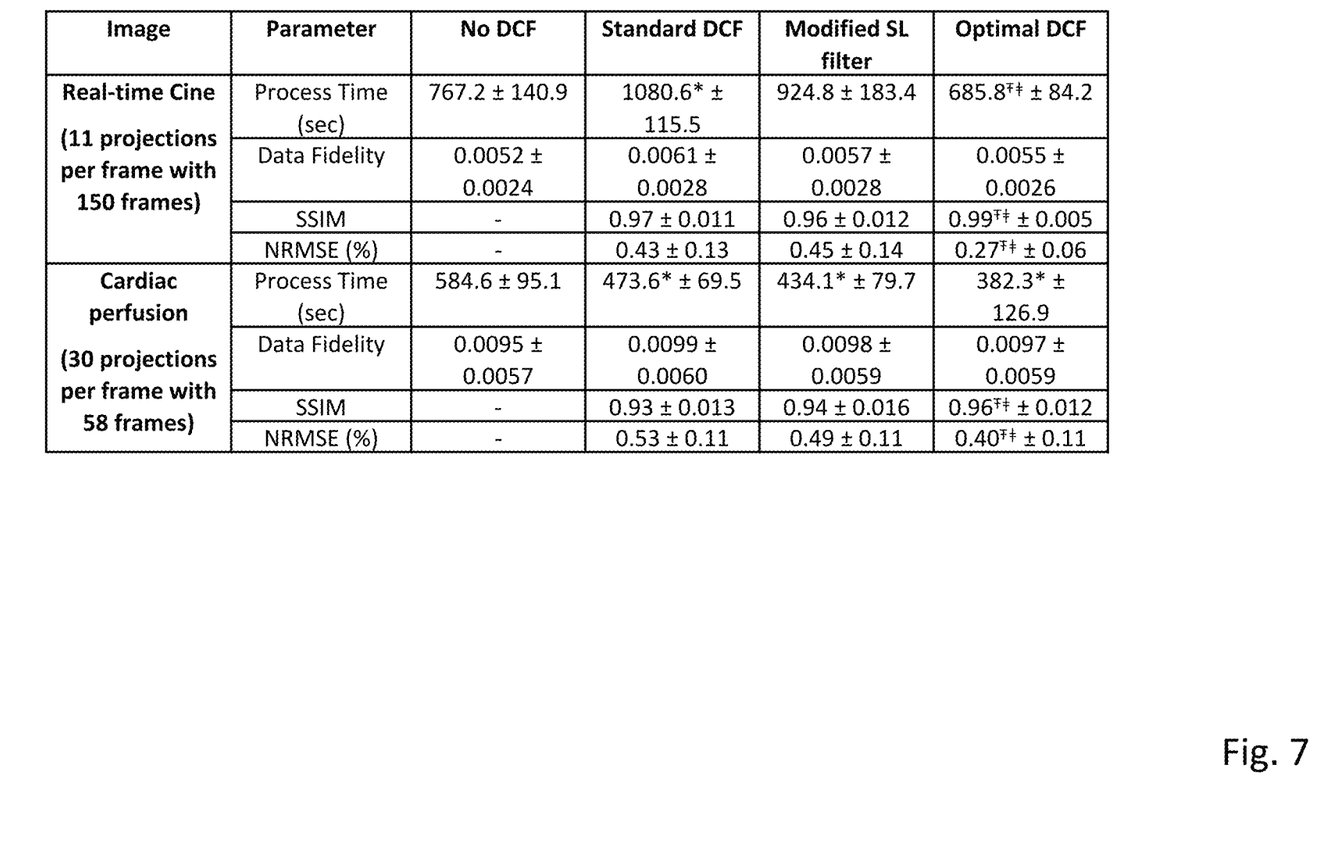
FIG. 7 is a table that summarizes the results of the analysis over 20 and 19 patients for real-time cine and cardiac perfusion, respectively, in accordance with an illustrative embodiment.

FIG. 7 is a table that summarizes the results of the analysis over 20 and 19 patients for real-time cine and cardiac perfusion, respectively, in accordance with an illustrative embodiment. As shown, for the subsampled real-time cine data with 11 radial projections per frame, the image quality metrics (NRMSE, SSIM) were significantly (p<0.05) better for optimal DCF than other DCFs, and the reconstruction time was faster for optimal DCF (685.8±84.2 sec [10.6% faster than no DCF]) than no DCF (767.2±140.9 sec), standard DCF (1080.6±115.5 sec [40.8% slower than no DCF]; p<0.05), and modified SL filter (924.8±183.4 sec [20.5% slower than no DCF]; p<0.05).

Figure 8:
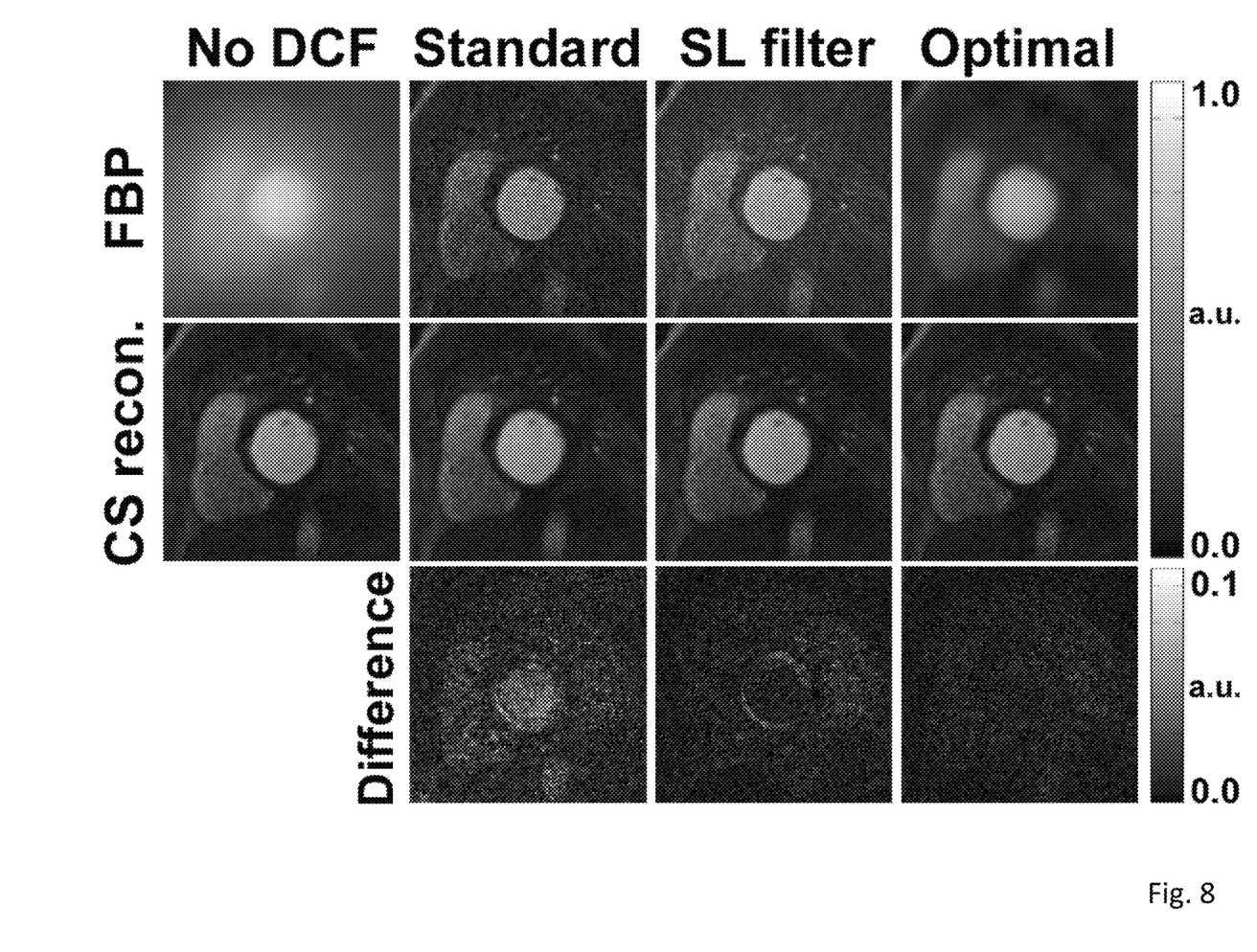
FIG. 8 depicts first-pass cardiac perfusion of a patient reconstructed using FBP (i.e., zero-filled NUFFT) and CS by four different DCFs (none [reference], standard, modified SL filter, optimal) in accordance with an illustrative embodiment.

FIG. 8 depicts first-pass cardiac perfusion of a patient reconstructed using FBP and CS by four different DCFs (none [reference], standard, modified SL filter, optimal) in accordance with an illustrative embodiment. FIG. 8 also shows the difference images compared with the reference. While all four reconstructions produced similar image quality, the difference images show that optimal DCF produced higher reconstruction accuracy than other DCFs. Summarizing the results over all 19 patients, for the subsampled cardiac perfusion data with 30 radial projections per frame, the image quality metrics (NRMSE, SSIM) were significantly (p<0.05) better for optimal DCF than other DCFs, and the reconstruction time was faster for optimal DCF (382.3±126.9 sec [34.6% faster than no DCF]) than no DCF (584.6±95.1 sec; p<0.05), standard DCF (473.6±69.5 sec [19.0% faster than no DCF]), and modified SL filter (434.1±79.7 sec [25.7% faster than no DCF]).

The above-described study describes a new framework for calculating an optimal DCF for fast CS reconstruction of subsampled radial k-space data. The DCF calculation is based on Nyquist distance along both radial and circumferential directions and the geometric properties of a polar coordinate system. The phantom experiment conducted at the Nyquist sampling rate demonstrates that our optimal DCF produces uniform densities in the gridded k-space, nearly as good as matching Cartesian k-space sampling. The patient MRI experiments demonstrate that the optimal DCF achieves faster CS reconstruction of subsampled radial k-space than other DCFs, verifying that DCF plays an important role in the processing time of CS reconstruction.

In principle, the proposed optimal DCF has the following advantages over an iterative DCF method. First, the optimal DCF produces a non-zero DC component, which is the most important component in k-space. Second, the optimal DCF calculation is computationally more efficient than the iterative method, because it is a straight-forward, analytical solution. Similarly, the optimal DCF calculation is faster than the Voronoi diagram method, which is computationally intensive. Compared with other non-zero DC methods, the optimal DCF also assigns a non-zero at the DC component and additionally calculates optimal density weights for samples nearby the DC component. Yet another DCF approach is to apply additional filters such as the SL filter, but at the expense of blurring. The SL filter was modified with a non-zero value at DC and its performance was tested. The results show that the optimal DCF outperformed this modified SL filter for accuracy and speed.

The optimal DCF can be extended to 3D radial projections by adapting a discrete unit surface area in a spherical coordinate system. With the added dimension, the discrete unit surface area in radial ($\Delta A_r$) and spherical ($\Delta A_s$) directions can be calculated. In radial direction, $\Delta A_r$ becomes 1 because the surface area of each sampled data point is the square of the discrete unit radial distance: $\Delta A_r = \Delta r \times \Delta r = 1$. Correspondingly, the discrete unit arc distance can be extended to a uniform surface area on the sphere: i.e., $\Delta A_r = \Delta A_s = 1$. For the measurement of the actual surface area between two neighboring data points, the Jacobian determinant from the conversion of spherical to Cartesian coordinate system can be used: i.e., $A_s = \iint r^2 \sin \varphi d\theta d\varphi = r^2 \Delta \theta \Delta \cos \varphi = 2\pi r^2(1-\cos \varphi')$, where $\varphi$ is a polar angle from the north pole in spherical coordinate system and $\varphi'$ is the measured angle between two radial projections. It was assumed that $2\pi r^2(1-\cos \varphi')$ can provide a consistent measurement of surface areas even though it may yield insufficient estimates; for example, the surface area between two projections, $Q_1(r, \theta_q, \varphi_{q1})$ and $Q_2(r, \theta_q, \varphi_{q2})$, is zero due to $\Delta \theta = 0$ in $r^2 \Delta \theta \Delta \cos \varphi$. Finally, DCF(r, $\theta_p$, $\varphi_p$) can be calculated in the same manner as DCF(r, $\theta_p$) described by Equations 4-5. The optimal DCF is applicable not only to 2D and 3D radial MRI but also to other medical (e.g., CT, SPECT, PET) and non-medical imaging modalities employing FBP and/or iterative reconstruction.

Any of the operations described herein can be performed by a computing system that includes a processor, memory, transceiver, interface, etc. The memory can store an operating system and computer-readable instructions. Upon execution by the processor, the computer-readable instructions implement the operations described herein. The transceiver is used to receive/transmit data, and the interface allows a user to program and control the system.

Figure 9:
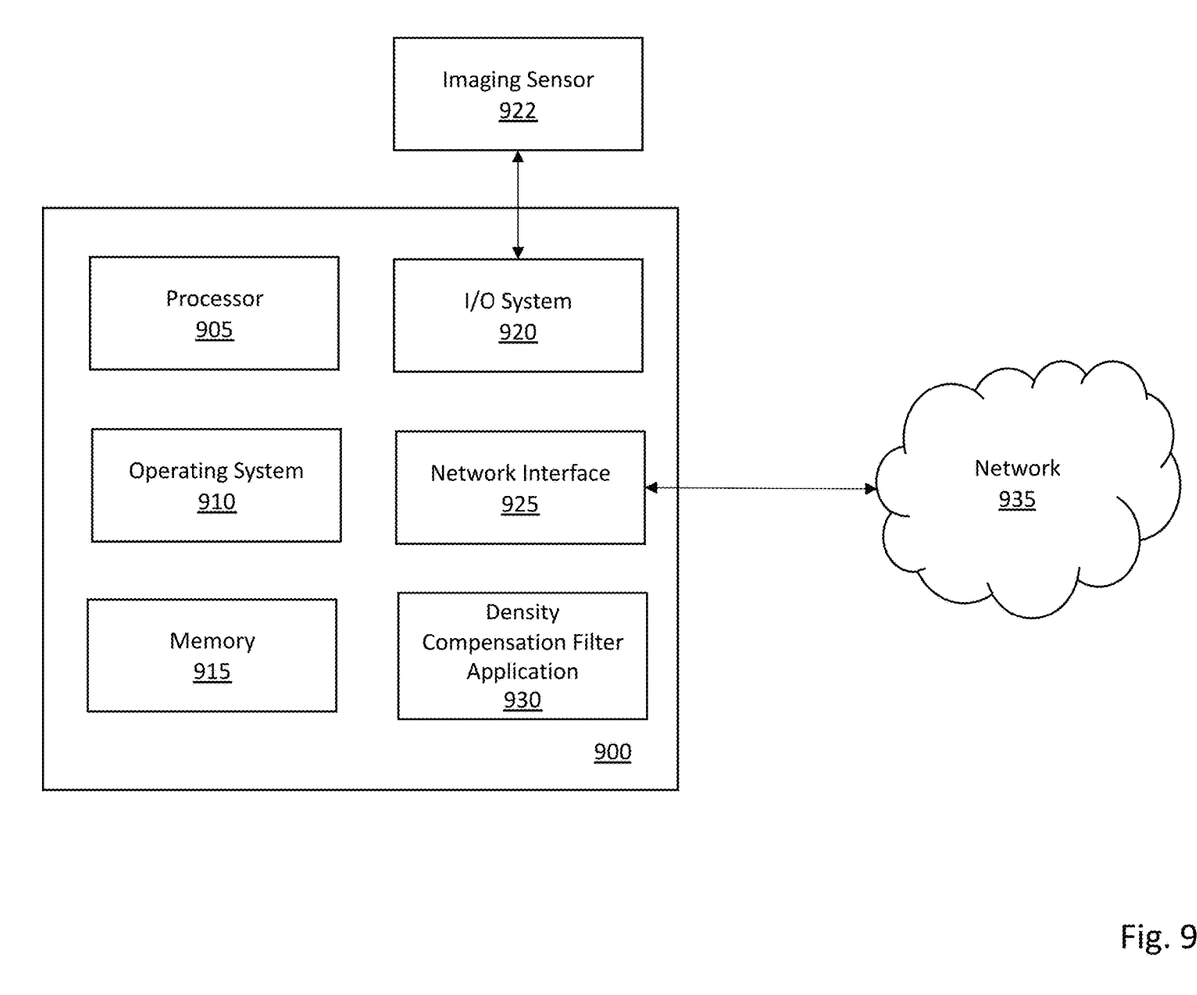
FIG. 9 is a block diagram of a computing device in communication with a network in accordance with an illustrative embodiment.

As an example, FIG. 9 is a block diagram of a computing device 900 in communication with a network 935 in accordance with an illustrative embodiment. The computing device 900 can be an imaging system or part of an imaging system in an illustrative embodiment. The computing device 900 includes a processor 905, an operating system 910, a memory 915, an input/output (I/O) system 920, a network interface 925, and a density compensation filter application 930. In alternative embodiments, the computing device 900 may include fewer, additional, and/or different components. The components of the computing device 900 communicate with one another via one or more buses or any other interconnect system. The computing device 900 can be any type of networked computing device such as a laptop computer, desktop computer, smart phone, tablet, workstation, server, etc. As shown, the computing device 900 is in communication with an imaging sensor 922. In some embodiments, the computing device 900 can be incorporated into an imaging system that includes the imaging sensor 922.

The processor 905 can be used to perform any of the calculations/operations described herein, and can be used to control the imaging sensor 922 and/or any of the other computing components. The processor 905 can be any type of computer processor known in the art, and can include a plurality of processors and/or a plurality of processing cores.

The processor 905 can include a controller, a microcontroller, an audio processor, a graphics processing unit, a hardware accelerator, a digital signal processor, etc. Additionally, the processor 905 may be implemented as a complex instruction set computer processor, a reduced instruction set computer processor, an x86 instruction set computer processor, etc. The processor 905 is used to run the operating system 910, which can be any type of operating system.

The operating system 910 is stored in the memory 915, which is also used to store programs, user data, network and communications data, peripheral component data, the density compensation filter application 930, and other operating instructions. The memory 915 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 920 is the framework which enables users and peripheral devices to interact with the computing device 900. The I/O system 920 can include a mouse, a keyboard, one or more displays, a speaker, a microphone, etc. that allow the user to interact with and control the computing device 900. The I/O system 920 also includes circuitry and a bus structure to interface with peripheral computing devices such as power sources, USB devices, data acquisition cards, peripheral component interconnect express (PCIe) devices, serial advanced technology attachment (SATA) devices, high definition multimedia interface (HDMI) devices, proprietary connection devices, etc.

The I/O system 920 also allows the computing device 900 to communicate with the imaging sensor 922. Specifically, the I/O system 920 provides operating instructions to the imaging sensor 922 and receives images and other data captured by the imaging sensor 922. The imaging sensor 922 can be any type of camera or image sensor, such as an MRI sensor, a CT sensor, a SPECT sensor, a PET sensor, etc. The imaging sensor 922 can include one or more light sources, one or more lenses, and additional optical components that enable the capture of images and associated data. In some embodiments, the I/O system 920 includes a transceiver having a transmitter and a receiver to facilitate the communication with components such as the imaging sensor 922. Alternatively, the transceiver may be incorporated into the network interface 925.

The network interface 925 includes transceiver circuitry that allows the computing device 900 to transmit and receive data to/from other devices such as remote computing systems, servers, websites, etc. The network interface 925 enables communication through a network 935, which can be one or more communication networks. The network 935 can include a cable network, a fiber network, a cellular network, a wi-fi network, a landline telephone network, a microwave network, a satellite network, etc. The network interface 925 also includes circuitry to allow device-to-device communication such as Bluetooth® communication. As an example, the network interface 925 can receive imaging data from a remote or local imaging sensor (e.g., the imaging sensor 922), where the imaging data includes k-space (or projection) data that results from an MRI (or other) scan of a patient or object.

The density compensation filter application 930 can include software in the form of computer-readable instructions which, upon execution by the processor 905, performs any of the various operations described herein for developing, implementing, and using a density compensation filter to perform imaging. The density compensation filter application 930 can utilize the processor 905 and/or the memory 915 as discussed above. In an alternative implementation, the density compensation filter application 930 can be remote or independent from the computing device 900, but in communication therewith.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An imaging system comprising:
   a sensor configured to receive imaging data, wherein the imaging data comprises k-space data from a magnetic resonance imaging (MRI) scan of a patient;
   a processor operatively coupled to the sensor and configured to:
   identify a degree of interaction between measured points of the k-space data located at a radius from a center of k-space;
   determine, based at least in part on the degree of interaction between the measured points, density weights for a density compensation filter;
   apply the density compensation filter to the k-space data to generate filtered k-space data;
   generate an MRI image of the patient based at least in part on the filtered k-space data; and
   convert the filtered k-space data from a polar coordinate system to a Cartesian coordinate system using gridding, wherein the conversion results in filtered and gridded k-space data with uniform density weights across k-space, and wherein the processor performs a Fourier transform to generate the MRI image of the patient based at least in part on the filtered and gridded k-space data.

2. The system of claim 1, wherein the processor is further configured to generate the MRI image of the patient using an inverse non-uniform Fourier transform based at least in part on the filtered and gridded k-space data.

3. The system of claim 1, wherein the degree of interaction is based at least in part on an arc distance between the measured points at the radius.

4. The system of claim 1, wherein the degree of interaction is based at least in part on a distance criterion, and wherein the distance criterion is Nyquist distance or 1.

5. The system of claim 1, wherein the k-space data is received in the form of a 2-dimensional or 3-dimensional Fourier transform.

6. An imaging system comprising:
   a sensor configured to receive imaging data, wherein the imaging data comprises projection data for a computed tomography (CT) scan, a single-photon emission computerized tomography (SPECT) scan, or a positron emission tomography (PET) scan of a patient;
   a processor operatively coupled to the sensor and configured to:
   identify a degree of interaction between measured points of the projection data located at a radius from a center of a projection space;
   determine, based at least in part on the degree of interaction between the measured points, density weights for a density compensation filter;
   apply the density compensation filter to the projection data to generate filtered projection data; and
   convert the filtered projection data from a polar coordinate system to a Cartesian coordinate system by way of gridding, wherein the conversion results in filtered and gridded projection data; and
   perform a transform to generate a CT image, a SPECT image, or a PET of the patient based at least in part on the filtered and gridded projection data.

7. The system of claim 6, wherein the transform comprises an inverse Radon transform.

8. The system of claim 6, wherein the degree of interaction is based at least in part on an arc distance between the measured points at the radius.

9. The system of claim 6, wherein the degree of interaction is based at least in part on a distance criterion, wherein the distance criterion is a sensor-to-sensor distance or 1.

10. The system of claim 9 wherein the sensor-to-sensor distance comprises a distance between two consecutive sensors in a 1-dimensional sensor array to receive the projection data.

11. The system of claim 6, wherein the projection data is received in the form of a 2-dimensional or 3-dimensional Radon transform.

12. A method for reconstructing an image, the method comprising:
   receiving, by a transceiver of a computing system, imaging data, wherein the imaging data comprises k-space data or projection data resulting from a scan of a patient;
   identifying, by a processor of the computing system, a degree of interaction between measured points of the k-space data or measured points of the projection data;
   determining, by the processor and based at least in part on the degree of interaction between the measured points, density weights for a density compensation filter;
   applying, by the processor, the density compensation filter to the projection data to generate filtered projection data or to the k-space data to generate filtered k-space data; and
   converting, by the processor, the filtered projection data or the filtered k-space data from a polar coordinate system to a Cartesian coordinate system by way of gridding, wherein the conversion results in filtered and gridded projection data or filtered and gridded k-space data with uniform density weights across k-space; and
   performing, by the processor, a Fourier transform based at least in part on the filtered and gridded k-space data or a Radon transform based at least in part on the filtered and gridded projection data to generate an image of the patient.

13. The method of claim 12, wherein the Fourier transform comprises an inverse non-uniform Fourier transform and the Radon transform comprises an inverse Radon transform.

14. The method of claim 12, wherein determining the degree of interaction includes determining an arc distance between the measured points at the radius.

15. The method of claim 12, wherein determining the degree of interaction includes determining a distance criterion, and wherein the distance criterion is 1 in a discrete environment.

\* \* \* \* \*

UNITED STATES PATENT AND TRADEMARK OFFICE
CERTIFICATE OF CORRECTION

Page 1 of 1

PATENT NO. : 11,893,662 B2
APPLICATION NO. : 17/393061
DATED : February 6, 2024
INVENTOR(S) : Kyungpyo Hong et al.

It is certified that error appears in the above-identified patent and that said Letters Patent is hereby corrected as shown below:

In the Specification

<u>Column 1, Lines 14-18:</u>
Delete the phrase:
"This invention was made with government support under R01HL116895, R01HL138578, R21EB024315, R21AG055954, R01HL151079, R01HL117888, and R21EB030806 awarded by the National Institutes of Health (NIH). The government has certain rights in the invention."
And replace with:
--This invention was made with government support under HL116895 awarded by the National Institutes of Health. The government has certain rights in the invention.--.

Signed and Sealed this
First Day of April, 2025

Coke Morgan Stewart
*Acting Director of the United States Patent and Trademark Office*